United States Patent [19]

Nobuhara et al.

[11] Patent Number: 4,680,261

[45] Date of Patent: Jul. 14, 1987

[54] PROCESS FOR PRODUCING INTERFERON

[75] Inventors: Masahiro Nobuhara, Iwatsuki; Toshinori Kanamori, Kasukabe; Kiyoshi Yamaguchi, Kawaguchi; Ei Mochida, Toshima, all of Japan

[73] Assignee: Mochida Pharmaceutical Co., Ltd., Tokyo, Japan

[21] Appl. No.: 645,761

[22] Filed: Aug. 30, 1984

[30] Foreign Application Priority Data

Sep. 17, 1983 [JP] Japan ................. 58-171733

[51] Int. Cl.⁴ .................. C12P 21/00; A61K 45/02
[52] U.S. Cl. ........................ 435/68; 435/811; 424/85
[58] Field of Search ............ 435/68, 811, 240, 244; 424/85

[56] References Cited

U.S. PATENT DOCUMENTS

| | | | |
|---|---|---|---|
| 4,007,086 | 2/1977 | Hamilton | 435/65 |
| 4,144,126 | 3/1979 | Burbidge | 435/240 |
| 4,460,685 | 7/1984 | Vilcek et al. | 424/85 |

OTHER PUBLICATIONS

Siegel, "Enhancement of Interferon Production by Poly(rI):Poly(rC) in Mouse Cell Cultures by Ascorbic Acid", Nature 254, pp. 531–532 (1975).

Askarkhodzhaev et al, "Stimulation of Interferon Production", Antibiotiki 24(9), pp. 669–672 (1979) C.A. 92:4565k.

Povolotskii et al, "Effects of Dibazole and Ascorbid Acid on the Antiviral Activity of Human Interferon in Cell Culture", Antibiotiki 24(4), pp. 291–294 (1979) C.A. 91: 32709h.

Dahl, et al, "The Effect of Ascorbic Acid on Production of Human Interferon and the Antiviral Activity in Vitro", Acta Pathol. Microbiol. Scand. Sect B, Microbiol: 84B(5), pp. 280–284 (1976) C.A. 85: 153793.

Blach et al, "Increase in L929 Cell Interferon Production in Serum-Free Medium", Arch. Immunol. Ther. Expl. 30(1–2), pp. 39–41 (1982) C.A. 98:33030m.

Psukas et al, "Kitchen Tricks with Ribonucleoside-Vanadyl Complexes", Federation Proceedings 41(4), p. 1204 Abst. #5452 (1982).

Berger et al, "Characterization of Interferon Massenger RNA Synthesis in Namalva Cells", Journal of Biological Chemistry 255(7), pp. 2955–2961 (1980).

Puskas et al, "Effect of Ribbonucleoside-Vanadyl Complexes on Enzyme Catalysed Reactions Central to Recombinant DNA Technology", Biochemistry 21, pp. 4602–4608 (1982).

Stewart, "The Interferon System", Springer-Verlag, NY (1981) pp. 97–103.

Stewart et al, "Interferons and Their Actions", CRC Press Inc. (1979) pp. 39–46.

*Primary Examiner*—Charles F. Warren
*Assistant Examiner*—John E. Tarcza
*Attorney, Agent, or Firm*—Parkhurst & Oliff

[57] ABSTRACT

A process for producing interferon comprises culturing interferon-producing mammalian cells in a cell culture medium containing at least one compound selected from the group consisting of ascorbic acid, an ascorbic acid derivative and a vanadium compound. According to the process of the present invention, interferon can be produced in large amounts.

11 Claims, No Drawings

PROCESS FOR PRODUCING INTERFERON

BACKGROUND OF THE INVENTION

The present invention relates to a process for producing interferon which comprises culturing an interferon-producing mammalian cell in a cell culture medium containing at least one compound selected from the group consisting of ascorbic acid, an ascorbic acid derivative and a vanadium compound.

Interferon was discovered by Nagano et al (*Comnt. Rend. Soc. Biol.*, Vol. 148, page 1700, 1954) and Isaccs et al (Proc. Roy. Soc. Ser. B., Vol. 174, Page 258, 1957) and is reported to possess an anti-tumor effect in addition to an anti-viral effect (Gressor, I. et al., *B.B.A.*, Vol. 516, page 231, 1978). Accordingly, attention has been focused upon the possibility of utilizing interferon as a medical drug.

Presently, interferon is roughly classified into three groups, which are termed interferon-$\alpha$ ($\alpha$-IFN), interferon-$\beta$ ($\beta$-IFN) and interferon-$\gamma$ ($\gamma$-IFN), respectively (*Nature*, Vol. 286, page 110, 1980). $\alpha$-IFN is produced mainly by stimulating leukocytes with a virus, $\beta$-IFN is produced mainly by stimulating fibroblasts with double-stranded RNA or a virus, and $\gamma$-IFN is produced mainly by stimulating lymphocytes with a mitogen.

It is essential to devise a process for producing interferon on a large scale for evaluating interferon as a medical drug. Heretofore, production processes such as a super-induction process (*Antimicrob. Ag. Chemother.*, Vol. 2, page 476, 1972) in which $\beta$-IFN is produced in a large amount, etc. have been reported. Further, the so-called priming effect in which interferon is produced in a large amount by treating producing cells with a small quantity of interferon prior to interferon production has been provided for practical use in large scale production of $\alpha$-IFN and $\beta$-IFN.

However, satisfactory large scale production of interferon has not been realized with these processes. Therefore, development of a process for excellent, large scale production of interferon is desired.

SUMMARY OF THE INVENTION

An object of the present invention is to provide a process for producing interferon.

The present invention is directed to a process for producing interferon which comprises culturing an interferon-producing mammalian cell in a cell culture medium containing at least one compound selected from the group consisting of ascorbic acid, as ascorbic acid derivative and a vanadium compound.

According to the process of the present invention, interferon can easily be produced in large amounts.

DETAILED DESCRIPTION OF THE INVENTION

As a result of extensive investigations on the large scale production of interferon, it has been discovered that large amounts of interferon can be prepared by culturing an interferon-producing mammalian cell in a cell culture medium containing at least one compound selected from the group consisting of ascorbic acid, an ascorbic acid derivative and a vanadium compound.

The present invention is directed to a process for producing interferon which comprises culturing an interferon-producing mammalian cell in a cell culture medium containing at least one compound selected from the group consisting of ascorbic acid, an ascorbic acid derivative and a vanadium compound.

The present invention is generally conducted in the following manner. Upon conventional culturing of an interferon-producing mammalian cell in a growth medium, a priming medium, an induction medium or a production medium, a medium containing at least one compound selected from the group consisting of ascorbic acid, an ascorbic acid derivative and a vanadium compound is used in place of an ordinary medium.

L-ascorbic acid is preferred as the ascorbic acid used in the present invention. As the ascorbic acid derivatives, it is possible to use monovalent metal salts of ascorbic acid, for example, lithium salts, potassium salts and sodium salts, and divalent metal salts of ascorbic acid, for example, magnesium salts, calcium salts, strontium salts and barium salts; however monovalent metal salts are preferred. Of these monovalent metal salts, the sodium salts is particularly preferred. It is preferred that the content of ascorbic acid and derivatives thereof in the cell culture medium be in a range of from 1 to 500 mg/l, and preferably in a range of from 10 to 100 mg/l.

Preferred examples of vanadium compounds include vanadyl sulfate, monovalent metal salts or orthovanadate such as potassium orthovanadate and sodium orthovanadate, monovalent metal salts of metavanadate such as potassium metavanadate and sodium metavanadate, monovalent metal salts of decavanadate and ammonium metavanadate, with particular preference of monovalent metal salts of orthovanadate. Of the monovalent metal salts, the sodium salt is particularly preferred. It is preferred that the content of vanadium compounds in the cell culture medium be in a range of from 0.01 to 100 mg/l, and preferably in a range of from 0.1 to 10 mg/l.

The ascorbic acid, ascorbic acid derivatives and vanadium compounds may each be contained singly in the cell culture medium; however, the use of these compounds in combination results in greater effects.

Any growth medium, priming medium, induction medium or production medium can be used as the medium in which the ascorbic acid, ascorbic acid derivatives and/or vanadium compounds are incorporated. Further, the ascorbic acid, ascorbic acid derivatives and/or vanadium compounds may also be incorporated in these media in combinations of two or more thereof.

As the media in which ascorbic acid, ascorbic acid derivatives and/or vanadium compounds are incorporated, Eagle MEM and RPMI 1640 media are generally employed but other media, for example, a 199 medium, a Ham F12 medium, an L15 medium, a modified Dulbecco's medium and the like may also be used.

The ascorbic acid, ascorbic acid derivatives and vanadium compounds employed in the present process are commercially available compounds. For example, L-ascorbic acid, sodium L-ascorbate, sodium orthovanadate and sodium metavanadate manufactured by Wako Pure Chemical Industry Co., Ltd. (Tokyo, Japan) can be employed.

As the interferon-producing mammalian cells, human diploid cells such as MRC-5 cells, WI-38 cells, Flow 1000 cells, Flow 4000 cells, FS-4, FS-7 etc. and human peripheral leukocytes can be employed. In addition, it is possible to use human-induced heteroid cells such as Namalwa cells, MG-63 cells, CCRF-SB cells, CCRF-CEM cells, as well as cells induced from other animals, for example, RK-13 (induced from rabbit), MDCK cells (induced from dog), L929 cells (induced from mouse) and primary culture cells of various animals, etc.

These cells are accessible via, for example, the American Type Culture Collection or Dainippon Pharmaceutical Co., Ltd. (Osaka, Japan).

As inducing agents for inducing interferon subsequent to culturing the interferon-producing mammalian cells, conventional inducing agents, for example, poly(I):poly(C), Sendai virus, Newcastle disease virus, concanavaline A and other inducing agents such as chlamydia, rickettsia, mitogen, lipopolysaccharides, etc. can be employed.

As culture conditions in a growth medium, a priming medium, an induction medium or a production medium, it is sufficient to use conventional conditions heretofore known.

Next, the present invention will be described in more detail with reference to experiments and examples below; however, it is not limited thereto.

EXPERIMENT 1

MRC-5 cells (human diploid cell strain) were inoculated in a plastic Petri dish in an inoculation amount of $3 \times 10^4$ cells/cm$^2$, together with 10 ml of an Eagle's MEM (growth medium) containing 10% bovine serum followed by culturing at 37° C. under a 5% $CO_2$ atmosphere. After the cells reached confluent, the medium was exchanged with 5 ml of an Eagle's MEM (priming medium) supplemented with 0.1% (w/v) human serum albumin containing 100 units/ml of $\beta$-IFN followed by culturing overnight.

Then, poly(I):poly(C) and cycloheximide were added to the medium in final concentrations of 30 mg/l and 2 mg/l, respectively. Cultivation was performed for 5 hours. Further, actinomycin D was added thereto at a final concentration of 1 mg/l followed by cultivation for 2 hours. After the cells were washed with PBS$^-$ twice, 5 ml of an Eagle's MEM (production medium) supplemented with 0.1% (w/v) human serum albumin was exchanged therefor. After cultivation overnight, the titer of interferon in the culture medium was determined. The titer of interferon was measured by the CPE method using FL cells and Sindbis virus and expressed under international reference standard (G023-902-527) of interferon as a standard.

The influence on interferon production was examined by incorporating 20 mg/l of sodium L-ascorbate and/or 1 mg/l of sodium orthovanadate in a growth medium, a priming medium, an induction medium and/or a production medium. The results are shown in Table 1.

TABLE 1

| | Additive and Medium | | | Produced Amount of Interferon-$\beta$ (unit/ml) |
|---|---|---|---|---|
| Growth Medium | Priming Medium | Induction Medium | Production Medium | |
| no additive | no additive | no additive | no additive | 12,500 |
| sodium L-ascorbate | no additive | no additive | no additive | 18,200 |
| no additive | sodium L-ascorbate | no additive | no additive | 17,600 |
| no additive | no additive | sodium L-ascorbate | no additive | 16,500 |
| no additive | no additive | no additive | sodium L-ascorbate | 16,100 |
| sodium orthovanadate | no additive | no additive | no additive | 19,300 |
| no additive | sodium orthovanadate | no additive | no additive | 19,000 |
| no additive | no additive | sodium orthovanadate | no additive | 18,400 |
| no additive | no additive | no additive | sodium orthovanadate | 18,000 |
| sodium L-ascorbate and sodium orthovanadate | no additive | no additive | no additive | 23,800 |
| no additive | sodium L-ascorbate and sodium orthovanadate | no additive | no additive | 22,200 |
| no additive | no additive | sodium L-ascorbate and sodium orthovanadate | no additive | 21,000 |
| no additive | no additive | no additive | sodium L-ascorbate and sodium orthovanadate | 19,500 |
| sodium L-ascorbate | sodium L-ascorbate | sodium L-ascorbate | sodium L-ascorbate | 27,600 |
| sodium L-ascorbate | sodium L-ascorbate | sodium L-ascorbate | no additive | 25,500 |
| sodium L-ascorbate | sodium L-ascorbate | no additive | sodium L-ascorbate | 24,900 |
| sodium L-ascorbate | no additive | sodium L-ascorbate | sodium L-ascorbate | 23,900 |
| no additive | sodium L-ascorbate | sodium L-ascorbate | sodium L-ascorbate | 23,300 |
| sodium orthovanadate | sodium orthovanadate | sodium orthovanadate | sodium orthovanadate | 29,300 |
| sodium orthovanadate | sodium orthovanadate | no additive | no additive | 25,200 |
| sodium orthovanadate | no additive | sodium orthovanadate | no additive | 24,700 |
| sodium orthovanadate | no additive | no additive | sodium orthovanadate | 24,300 |
| no additive | sodium orthovanadate | sodium orthovanadate | no additive | 23,100 |
| no additive | sodium orthovanadate | no additive | sodium orthovanadate | 22,700 |
| no additive | no additive | sodium orthovanadate | sodium orthovanadate | 21,500 |
| sodium L-ascorbate | sodium orthovanadate | sodium L-ascorbate | sodium orthovanadate | 28,900 |
| sodium L-ascorbate and sodium orthovanadate | sodium L-ascorbate and sodium orthovanadate | sodium L-ascorbate and sodium orthovanadate | sodium L-ascorbate and sodium orthovanadate | 35,500 |

EXPERIMENT 2

In a spinner's flask, $5 \times 10^4$ cells/ml of Namalwa cells were inoculated together with 200 ml of RPMI 1640 medium (growth medium) containing 5% bovine serum. After cultivation for 3 days, priming was performed overnight using 200 ml of RPMI 1640 medium (priming medium) containing 100 units/ml of interferon-α and 0.1% (w/v) human serum albumin. Thereafter, Sedai virus was added to the medium at a final concentration of 100 HAU/ml. After cultivation overnight, the Sendia virus was inactivated at pH 2.0 and the titer of interferon-α in the medium was determined. The titer was measured by the CPE method and expressed using international reference standard (G023-901-527) of interferon as a standard.

The influence of various concentrations of sodium metavanadate incorporated in a growth medium on the production amount of interferon-α was examined and the results are shown in Table 2. Furthermore, the influence of various concentrations L-ascorbic acid incorporated in a priming medium on the production amount of α-IFN was examined and the results are shown in Table 3.

TABLE 2

| Final Concentration of Sodium Metavanadate Added to Growth Medium (mg/l) | Produced Amount of Interferon-α (unit/ml) |
| --- | --- |
| 0 (control) | 2,410 |
| 0.001 | 2,520 |
| 0.01 | 3,310 |
| 0.1 | 4,180 |
| 1 | 4,740 |
| 10 | 4,260 |
| 100 | 3,640 |
| 1000 | 2,190 |

TABLE 3

| Final Concentration of L-Ascorbic acid added to Priming Medium (mg/l) | Produced Amount of Interferon-α (unit/ml) |
| --- | --- |
| 0 (control) | 2,230 |
| 0.1 | 2,320 |
| 1 | 3,130 |
| 10 | 4,870 |
| 30 | 5,310 |
| 100 | 4,990 |
| 500 | 3,720 |
| 2000 | 1,950 |

EXPERIMENT 3

In a plastic flask having a culture area of 150 cm$^2$, 3×10$^6$ cells of L929 cells were inoculated together with 50 ml of a 199 medium (growth medium) containing 10% (v/v) of fetal calf serum and grown for 4 days to reach confluent. The medium was exchanged with 50 ml of a 199 medium containing 100 mg/l of poly (I):poly(C) and 0.01% (w/v) human serum albumin and after 5 hours, exchanged with 25 ml of a 199 medium (production medium) containing 0.01% (w/v) of human serum albumin. After culturing for 18 hours, the titer of interferon in the production medium was measured.

The influence of various vanadium compounds incorporated into the growth medium on the production amount of interferon was examined and the results are shown in Table 4.

TABLE 4

| Vanadium Compound Contained in Growth Medium (mg/l) | Produced Amount of Interferon (IU/ml) |
| --- | --- |
| none (control) | 630 |
| sodium orthovanadate 2 mg/l | 2,500 |
| vanadyl sulfate 2 mg/l | 1,120 |
| sodium decavanadate 2 mg/l | 1,730 |
| ammonium metavanadate 2 mg/l | 1,570 |

EXAMPLE 1

Production of α-IFN

Namalwa cells were inoculated at 3×10$^5$ cells/ml in RPMI 1640 medium supplemented with 5% (v/v) calf serum containing 40 mg/l of L-ascorbic acid and 3 mg/l of sodium metavanadate.

After the cells were cultured at 37° 1 C. for 3 days in a spinner's flask, the cells were collected by centrifuge. The cells were suspended in RPMI 1640 medium containing 0.1% (w/v) human serum albumin, 40 mg/l of L-ascorbic acid, 3 mg/l of sodium metavanadate and 100 units/ml of α-IFN followed by culturing overnight. Sendai virus was added to the medium in a final concentration of 100 HAU/ml followed by further culturing overnight. By centrifuge, the cells were eliminated and the pH of the resulting supernatant was adjusted to 2.0. By settling at 4° C. overnight, the Sendai virus was inactivated. The titer of α-IFN in the medium was 3,340 units/ml. The titer of α-IFN was 1820 units/ml when a medium containing neither L-ascorbic acid nor sodium metavanadate was used.

EXAMPLE 2

Production of β-IFN

MRC-5 cells (human diploid cell strain) were inoculated at 4×10$^4$ cells/ml in Eagle's MEM containing 10% (v/v) calf serum, 20 mg/l of L-ascorbic acid and 1 mg/l of sodium orthovanadate and cultured at 37° C. for 4 days. The medium was exchanged with an Eagle's MEM containing 0.1% (w/v) human serum albumin, 20 mg/l of sodium L-ascorbate, 1 mg/l of orthovanadate and 100 units/ml of interferon-β followed by cultivation overnight. Poly(I):poly(C), 30 mg/l and 2 mg/l of cycloheximide were added to the medium. After culturing for 5 hours, 2 mg/l of actinomycin D was added to the medium and the culture was performed for an additional 2 hours.

After the cultured cells were washed with PBS$^-$ twice, an Eagle's MEM containing 0.1% (w/v) human serum albumin was added to the cells and the culture was performed overnight. The titer of β-IFN in the medium was 35,300 units/ml. The titer of β-IFN was 10,200 units/ml when a medium containing neither sodium L-ascorbate nor sodium orthovanadate was used.

EXAMPLE 3

Production of γ-IFN

Fractions containing lymphoctyes were collected from peripheral blood of adult volunteers by the Ficoll-Hypaque gradient method. After culturing these cells in a plastic Petri dish, non-adhered cells were collected. The collected cells were suspended at 2×10$^6$ cells/ml in RPMI 1640 medium supplemented with 0.1% (w/v) human serum albumin containing 20 mg/l of sodium L-ascorbate and 2 mg/l of sodium metavanadate. To the suspension, concahavaline A was added in a concentration of 5 μg/ml followed by cultivation for 48 hours. After completion of the cultivation, the cells were removed by centrifuge. The titer of γ-IFN in the medium was determined by the CPE method using international reference standard (G023-901-527) of γ-IFN as a standard. As a result, the titer of γ-IFN in the medium was 2,930 units/ml. Further, the titer of γ-IFN was 680 units/ml when a medium containing neither sodium L-ascorbate nor sodium metavanadate was used.

While the invention has been described in detail and with reference to specific embodiments thereof, it will be apparent to one skilled in the art that various changes and modifications can be made therein without departing from the spirit and scope therof.

What is claimed is:

1. A process for producing interferon comprising, culturing an interferon-producing mammalian cell in a cell culture medium containing an inorganic vanadium compound, in an amount sufficient to enhance interferon production.

2. The process of claim 1, wherein the concentration of said vanadium compound is from 0.01 to 100 mg/l.

3. The process of claim 1, wherein said cell culture medium comprises at least one cell culture medium selected from the group consisting of a growth medium, a priming medium, an induction medium and a production medium.

4. The process of claim 1, wherein said interferon-producing mammalian cell is a human cell.

5. The process of claim 1, wherein said interferon-producing mammalian cell comprises at least one mammalian cell selected from the group consisting of MRC-5, WI-38, Flow 1000, Flow 4000, FS-4, FS-7, Namalwa, MG-63, CCRF-SB, CCRF-CEM and peripheral leukocytes.

6. The process of claim 1, wherein said interferon-producing mammalian cell is selected from the group consisting of RK-13, MDCK and L929.

7. The process of claim 1, wherein said vanadium compound comprises one compound selected from the group consisting of vanadyl sulfate, monovalent metal salts of orthovanadate, monovalent metal salts of metavanadate, monovalent metal salts of decavanadate and ammonium metavanadate.

8. The process of claim 7, wherein said vanadium compound is selected from the group consisting of sodium orthovanadate and potassium orthovanadate.

9. The process of claim 7, wherein said vanadium compound is selected from the group consisting of ammonium metavanadate, sodium metavanadate and potassium metavanadate.

10. The process of claim 7, wherein said monovalent metal salts of decavanadate are selected from the group consisting of sodium decavanadate and potassium decavanadate.

11. The process of claim 1, wherein the concentration of said vanadium compound is from 0.1 to 10 mg/l.

* * * * *